United States Patent [19]

Hasegawa

[11] Patent Number: 5,478,552
[45] Date of Patent: Dec. 26, 1995

[54] LIQUID COSMETIC COMPOSITION

[75] Inventor: Tomoko Hasegawa, Maebashi, Japan

[73] Assignee: Mitsubishi Pencil Kabushiki Kaisha, Tokyo, Japan

[21] Appl. No.: 271,857

[22] Filed: Jul. 7, 1994

[30] Foreign Application Priority Data

Jul. 16, 1993 [JP] Japan .................................. 5-177031

[51] Int. Cl.⁶ .................. A61K 7/021; A61K 7/025; A61K 47/00

[52] U.S. Cl. .................. 424/63; 424/64; 514/777; 514/949

[58] Field of Search ............ 424/63, 64; 514/949, 514/777

[56] References Cited

U.S. PATENT DOCUMENTS

| | | | |
|---|---|---|---|
| 4,637,933 | 1/1987 | Zabotto et al. | 514/949 |
| 5,085,855 | 2/1992 | Shore | 514/949 |
| 5,288,482 | 2/1994 | Krzyzsik | 514/949 |

FOREIGN PATENT DOCUMENTS

| | | | |
|---|---|---|---|
| 0331833 | 9/1989 | European Pat. Off. | 514/785 |
| 0440387A1 | 8/1991 | European Pat. Off. | 514/785 |
| 0504066A1 | 9/1992 | European Pat. Off. | 514/785 |
| 0522916A2 | 1/1993 | European Pat. Off. | 514/785 |
| 0526289A1 | 2/1993 | European Pat. Off. | 514/785 |
| 0596465A1 | 5/1994 | European Pat. Off. | 514/785 |
| 70.05646 | 11/1971 | France | 514/785 |
| 3837473A1 | 5/1990 | Germany | 514/785 |
| 61-207319 | 3/1985 | Japan | 424/63 |
| 5-32527 | 10/1986 | Japan | 424/63 |
| 61-236716 | 3/1991 | Japan | 424/63 |

*Primary Examiner*—Dale R. Ore
*Attorney, Agent, or Firm*—Darby & Darby

[57] ABSTRACT

A liquid cosmetic material having a viscosity of 100,000 cp or less is here disclosed which comprises trimethylsiloxysilicic acid, a volatile silicone, a sucrose fatty acid ester, and a member selected from the group consisting of silicic anhydride having hydrophobic-treated surface, a clay mineral having organic-treated surface and mixtures thereof. The liquid cosmetic material of the present invention is excellent in use feeling, water resistance after application, adhesive properties, dispersion properties of a liquid and fixing stability to skin.

9 Claims, 1 Drawing Sheet

LIQUID COSMETIC COMPOSITION

BACKGROUND OF THE INVENTION (1) Field of the Invention

The present invention relates to a liquid cosmetic material which is excellent in use feeling, water resistance after application, adhesive properties, dispersion properties of a liquid and fixing stability to skin. The liquid cosmetic material of the present invention is applicable to many uses, and it is particularly suitable for uses such as a lipstick, a foundation and an eye shadow.

(2) Description of Related Art

A variety of cosmetic materials has been prepared to improve water resistance, adhesive properties and the like as set forth below.

Japanese Patent Application Laid-open No. (Hei) 5-32527 discloses an amino-modified or an ammonium-modified polymeric silicone having a polymerization degree of 3,000 to 20,000 is blended with a cosmetic material containing optional components such as kaolin (kaolinite) and volatile silicone to obtain a cosmetic material for makeup in which water resistance, sweat resistance and oil resistance have been improved.

Japanese Patent Application Laid-open No. (Sho) 61-236716 discloses a lipstick composition containing a lipophilic gelling agent such as a lipophilic bentonite or a sucrose fatty acid ester for the purpose of lowering the viscosity and hardness of the lipstick composition to certain values or less.

In Japanese Patent Application Laid-open No. (Sho) 61-207319, it is disclosed that a cosmetic material containing an oil and a dehydrated clay mineral is blended with a starch fatty acid ester to obtain the cosmetic material which can keep up a good use feeling and which can inhibit oil float during use.

In the above-mentioned cosmetic materials, it is intended to improve water resistance after application to skin, dispersion properties and fixing stability to skin, but in fact, these effects are not sufficient.

That is, the cosmetic material disclosed in Japanese Patent Application Laid-open No. (Hei) 5-32527 does not have the sufficiently stable dispersion properties, and the lipstick composition disclosed in Japanese Patent Application Laid-open No. (Sho) 61-236716 is still poor in the stability of dispersion properties, fixing properties to skin and water resistance. In addition, with regard to the cosmetic material disclosed in Japanese Patent Application Laid-open No. (Sho) 61-207319, any of the stability of dispersion properties, water resistance and fixing properties to skin are not sufficiently satisfactory.

SUMMARY OF THE INVENTION

Therefore, an object of the present invention is to provide a liquid cosmetic material which is excellent in use feeling, water resistance after application, adhesive properties, dispersion properties of a liquid and fixing stability to skin.

In one aspect, the present invention provides a liquid cosmetic material which comprises trimethylsiloxy-silicic acid, a volatile silicone, a sucrose fatty acid ester, and a member selected from the group consisting of silicic anhydride having hydrophobic-treated surface, a clay mineral having organic-treated surface and mixtures thereof, the liquid cosmetic material having a viscosity of 100,000 cp or less.

In another aspect, the present invention provides an application instrument which comprises a reservoir containing a liquid cosmetic material comprising trimethylsiloxy-silicic acid, a volatile silicone, a sucrose fatty acid ester, and a member selected from the group consisting of silicic anhydride having hydrophobic-treated surface, a clay mineral having organic-treated surface and mixtures thereof, the liquid cosmetic material having a viscosity of 100,000 cp or less.

Further advantages and features of the present invention as well as the scope, nature and utilization of the present invention will become apparent to those skilled in the art from the description of the preferred embodiments of the present invention set forth below.

DESCRIPTION OF THE PREFERRED EMBODIMENTS

Figure 1:
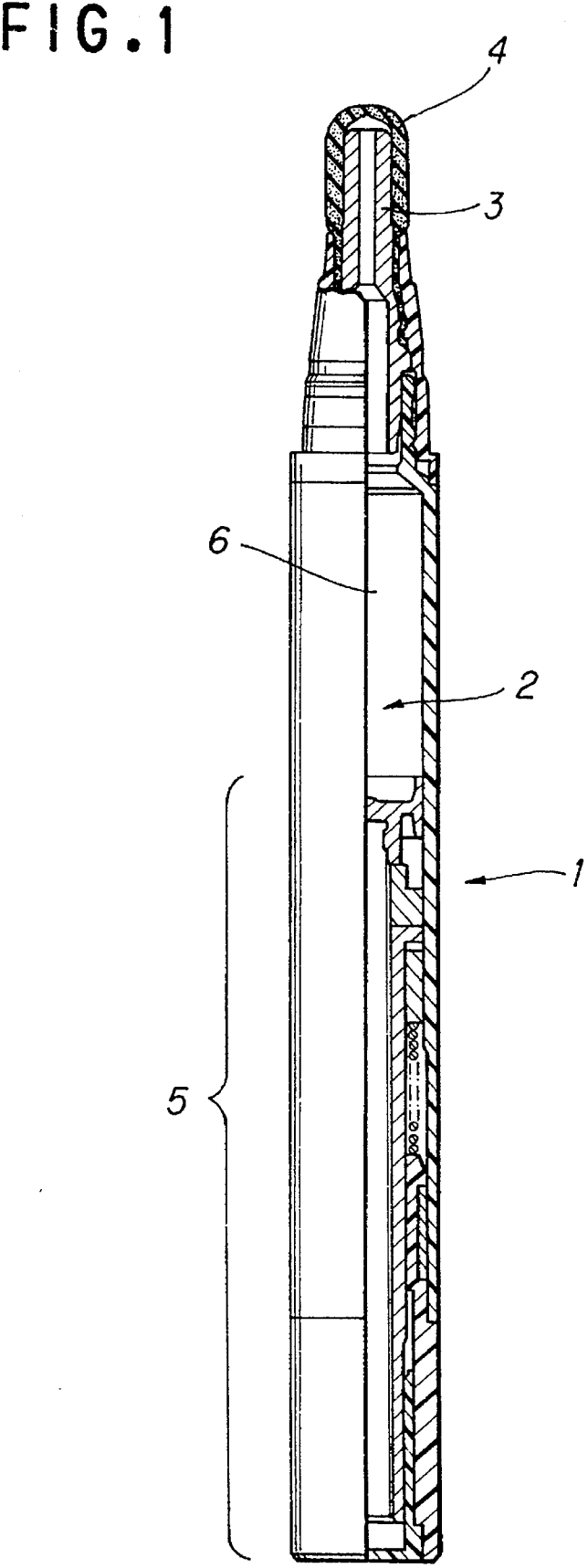
FIG. 1 shows a longitudinal partial cross-sectional view of an application instrument within the present invention.

Now, the present invention will be described in detail. Incidentally, the content of each component described in this specification means its content in 100 parts by weight of an obtained liquid cosmetic material.

As described above, one aspect of the present invention is directed to an improved liquid cosmetic material. This liquid cosmetic material is a composition comprising trimethylsiloxysilicic acid, a volatile silicone, a sucrose fatty acid ester, and a member selected from the group consisting of silicic anhydride having hydrophobic-treated surface, a clay mineral having organic-treated surface and mixtures thereof, the liquid cosmetic material having a viscosity of 100,000 cp or less.

Trimethylsiloxysilicic acid is a compound for imparting excellent fixing properties after application and pigment dispersing properties, and the amount of trimethylsiloxysilicic acid to be blended is in the range of 0.2 to 50 parts by weight, preferably 2 to 20 parts by weight.

If the amount of trimethylsiloxysilicic acid is less than 0.2 part by weight, fixing properties after application and pigment dispersing properties cannot be sufficiently exerted, and if it is more than 50 parts by weight, the spread of the cosmetic material is poor, so that stiff feeling and stretch feeling remain unpreferably.

The volatile silicone is excellent in fluidity at the time of the application, and after application, it volatilizes, thereby preventing cosmetic gather and imparting good adhesive properties. The amount of the volatile silicone to be blended is in the range of 5 to 80 parts by weight, preferably 10 to 60 parts by weight.

If the amount of the volatile silicone is less than 5 parts by weight, there cannot be obtained sufficient fluidity at the time of application, the prevention of cosmetic gather after the application and good adhesive properties. Conversely, if it is more than 80 parts by weight, the volatilization stagnates, which causes the cosmetic gather unpreferably. Representative examples of volatile silicones include octamethylcyclotetrasiloxane, decamethylcyclopentasiloxane, dodecamethylcyclohexasiloxane, hexamethylcyclotrisiloxane and low molecular weight polymethylsiloxane.

The sucrose fatty acid ester can impart dispersion stability and fixing stability to skin. Examples of the sucrose fatty acid ester include sucrose fatty acid monoester, diester, triester, tetraester, pentaester, hexaester, heptaester and octaester, and these sucrose fatty acid esters can be used singly or in combination.

In the present invention, fatty acids used for esterification of sucrose include saturated fatty acids or unsaturated fatty acids having 1 to 28 carbon atoms.

The amount of the sucrose fatty acid ester to be blended is in the range of 1 to 20 parts by weight, preferably 2 to 10 parts by weight. If the amount of the sucrose fatty acid ester is less than 1 part by weight, the dispersion stability and the fixing stability to the skin cannot be imparted to the resulting cosmetic material, and conversely, if it is more than 20 parts by weight, the viscosity thereof becomes unpreferably too high, and a film obtained by application has no flexibility.

Silicic anhydride having hydrophobic-treated surface means the silicic anhydride whose surface is made hydrophobic, and a clay mineral having organic-treated surface means the clay mineral whose surface is subjected to an organic treatment. The silicic anhydride having hydrophobic-treated surface and the clay mineral having organic-treated surface can both impart the dispersion stability and the fixing stability to skin. They can be used singly or in combination together with the abovementioned three components. The amount of the silicic anhydride and/or the clay mineral to be blended is in the range of 0.5 to 50 parts by weight, preferably from 2 to 20 parts by weight. If the amount of one or both of the silicic anhydride and the clay mineral is less than 0.5 part by weight, the dispersion stability cannot be imparted to the resulting cosmetic material, and if it is in excess of 50 parts by weight, the viscosity thereof becomes unpreferably too high.

One example of silicic anhydrides having hydrophobic-treated surface is silicic anhydride whose surface has been treated with silicone. Representative examples of silicones used for hydrophobic treatment include polymethylhydrogensiloxane, polymethylsiloxane and polymethylphenylsiloxane. These silicones may be used singly or in combination.

The clay mineral having organic-treated surface may be produced by baking surface of the clay mineral with a cationic surface active agent or an organic silicone to add an organic compound to the surface of the clay mineral. Representative examples of clay minerals include bentonite, talc, kaolin (kaolinite), mica, clay, sericite, hectorite, montmorillonite and smectite. In the present invention, there are preferably used bentonite, hectorite and montmorillonite. These clay minerals can be used singly or in combination.

Representative examples of the cationic surface active agents which can be used to apply the organic treatment to the surface of the clay mineral include benzyldimethylstearylammonium chloride, dimethyldiacetostearylammonium chloride, distearyldimethylammonium chloride and benzalkanium chloride. These cationic surface active agents can be used singly or in combination.

Representative examples of silicones used for baking the surface of the clay mineral include polymethylhydrogensiloxane, polymethylsiloxane and polymethylphenylsiloxane. These silicones may be used singly or in combination.

The liquid cosmetic material of the present invention has a viscosity of 100,000 cp or less, preferably 70,000 cp or less, more preferably 30,000 to 70,000 cp.

If the viscosity is in excess of 100,000 cp, the effect of the liquid cosmetic material of the present invention cannot be sufficiently exerted.

The liquid cosmetic material of the present invention can be blended with components which can be used in a usual cosmetic material in compliance with the use purpose of a lipstick, a foundation, an eye shadow or the like, in addition to the above-mentioned components. Examples of such additional components include oils, surface active agents, pigments and perfumes, and they can be blended, so long as the effect of the present invention is not impaired.

The other aspect of the present invention is directed to an application instrument comprising a reservoir containing a specific liquid cosmetic material. This application instrument comprises reservoir containing a liquid cosmetic material comprising trimethylsiloxysilicic acid, a volatile silicone, a sucrose fatty acid ester, and a member selected from the group consisting of silicic anhydride having hydrophobic-treated surface, a clay mineral having organic-treated surface and mixtures thereof, and the liquid cosmetic material having a viscosity of 100,000 cp or less.

FIG. 1 shows an example of the application instrument which can be used for the liquid cosmetic material of the present invention. The application instrument 1 includes a reservoir 2 containing a liquid cosmetic material 6, an ejective portion 3 capable of discharging the liquid cosmetic material 6 forwarded by a rotational extruding means 5, and an applicator 4 from which the liquid cosmetic material 6 can ooze at the tip of the application instrument 1. The rotational extruding means may be replaced with pushing means. The preferable ejective portion is provided with a tube having an internal diameter of 0.5 to 3 mm, and this ejective portion, when used, can be molded into a length in accordance with the structure of the application instrument. As the material of the ejective portion, stainless steel is most suitable from the viewpoints of anticorrosion, cost, workability, strength and the like, but the molded article of a resin can be also used.

As the applicator of the application instrument, for example, a continuously porous and flexible foam is desirable, but the applicator may be any of other members inclusive of a brush. Examples of such an applicator are commercially available urethane foams such as the trade names "Everlight SF HR-20 to 50" and "Everlight HF" made by Bridgestone Co., Ltd.

When this applicator is the continuously porous and flexible foam, the viscosity of the liquid cosmetic material of the present invention is adjusted to 100,000 cp or less, preferably 50 to 100,000 cp so that the pores in the foam may retain a necessary and suitable amount of the cosmetic material. As a result, at the time of application, the retained liquid cosmetic material can be applied onto skin in a suitable state. In this case, it is more preferable that the ejective portion has a tube having an internal diameter of 1 mm and the viscosity of the liquid cosmetic material is in the range of 500 to 70,000 cp.

The above-mentioned cosmetic material of the present invention can substantially solve problems of a conventional cosmetic material. That is, the liquid cosmetic material of the present invention can improve use feeling, water resistance after application, adhesive properties, dispersion properties of a liquid and fixing stability to skin.

The liquid cosmetic material of the present invention can be used in the application instrument which comprises a reservoir containing the liquid cosmetic material therein, an ejective portion capable of discharging the liquid cosmetic material forwarded by a pushing or a rotational extruding means, and an applicator from which the liquid cosmetic material can ooze at the tip of the application instrument. In this case, the durability of the liquid in the applicator is good, and the use feeling of the cosmetic material to skin is excellent.

Additionally, also in the case that the liquid cosmetic material of the present invention is spread on skin by a puff, a brush or a finger, the good using feeling can be obtained.

Next, the present invention will be described in more detail with reference to examples and comparative examples, but the scope of the present invention should not be limited to there examples at all.

EXAMPLES

Examples 1 to 3, Comparative Examples 1 to 4

Liquid cosmetic materials (eye shadows) were prepared in accordance with blend ratios shown in Table 1. For the respective liquid cosmetic materials, a sensual evaluation was made in points of use feeling, cosmetic gather, adhesive properties (water resistance) and stability with time by 20 test panels. The results are shown in Table 1.

For the liquid cosmetic materials prepared in Examples 1 to 3 and Comparative Examples 1 to 4, viscosity, use feeling, cosmetic gather, adhesive properties (water resistance) and stability were measured and evaluated by the following procedures.

(1) Measurement of viscosity

The viscosity was measured at a rotational speed of 0.5 rpm by the use of a cone plate type E model viscometer EHD (made by Toki Sangyo Co., Ltd.).

(2) Use feeling

This sensual evaluation was made from a state at the time of application on the basis of the following ranking:

o: Good.

Between "good" and "bad".

x: Bad.

(3) Cosmetic gather

This sensual evaluation was made from a state after application to skin (after 30 minutes or after 3 hours) on the basis of the following ranking:

o: A case where cosmetic gather was not present.

x: A case where cosmetic gather was present.

(4) Adhesive properties (water resistance)

This sensual evaluation was made from an adhesive state of the cosmetic material to a tissue paper at the time of light wipe with the wet tissue paper 10 minutes after the application on the basis of the following ranking:

o: A case where the cosmetic material did not adhere to the tissue paper.

x: A case where the cosmetic material adhered to the tissue paper.

(5) Stability with time

Each of prepared liquid cosmetic materials was placed in a settling tube having a diameter of 2 cm, and after one week and one month, a separated supernatant liquid was visually observed. Evaluation was made on the basis of the following ranking:

o: A case where no supernatant liquid was present.

a: A case where the supernatant liquid was slightly present.

x: A case where the transparent supernatant liquid was present.

From the results in Table 1, the following facts have been clarified.

Comparative Examples 1 to 4 are outside the scope of the present invention. Comparative Example 1 shows a liquid cosmetic material containing neither silicic anhydride having hydrophobic-treated surface nor a clay mineral having organic-treated surface. Comparative Example 2 shows a liquid cosmetic material prepared by adding the silicic anhydride to the liquid cosmetic material of Comparative Example 1. Comparative Example 3 shows a liquid cosmetic material containing no trimethylsiloxysilicic acid. Comparative Example 4 shows a liquid cosmetic material containing no sucrose fatty acid ester.

It is apparent from the results of Comparative Examples 1 to 4 that liquid cosmetic materials not containing any of trimethylsiloxysilicic acid, a volatile silicone, a sucrose fatty acid ester, and a member selected from the group consisting of silicic anhydride having hydrophobic-treated surface, a clay mineral having organic-treated surface and mixtures thereof are devoid of the total balance of use feeling, cosmetic gather, adhesive properties (water resistance) and stability.

On the contrary, the liquid cosmetic materials of Examples 1 to 3 contain all of the components prescribed in the present invention, and it is apparent that they are excellent in all of use feeling, cosmetic gather, adhesive properties (water resistance) and stability.

TABLE 1

| | Comparative Example | | | |
|---|---|---|---|---|
| | 1 | 2 | 3 | 4 |
| Blend Ratio (parts by weight)*5 | | | | |
| Silicic anhydride | — | 6 | — | — |
| Hydrophobic silica*1 | — | — | 6 | 6 |
| Trimethylsiloxysilicic acid*2 | 9 | 9 | — | 9 |
| 1,3-butanediol | 1 | 1 | 1 | 1 |
| Neopentyl glycol dioctanoate | 3 | 3 | 3 | 3 |
| Nylon powder | 8 | 8 | 8 | 8 |
| Inorganic pigment | 2 | 2 | 2 | 2 |
| Mica titanium | 20 | 20 | 20 | 20 |
| Liquid paraffin | 2 | 2 | 2 | 2 |
| Sucrose fatty acid ester*6 | 6 | 6 | 6 | — |
| Parabens | 2 | 2 | 2 | 2 |
| Clay mineral*3 | — | — | — | — |
| Decamethylcyclopentasiloxane*4 | 47 | 41 | 50 | 47 |
| Viscosity (cp) | 20,000 | 60,000 | 70,000 | 20,000 |
| Eavaluation | | | | |
| Use feeling | Δ | Δ | x | x |
| Cosmetic gather | | | | |
| after 30 min | o | o | x | o |
| after 6 hr | o | o | x | o |
| Adhesive properties (water resistance) | o | o | x | o |
| Stability (40° C.) | | | | |
| after 1 week | x | Δ | Δ | x |
| after 1 month | x | x | Δ | x |

| | Example | | |
|---|---|---|---|
| | 1 | 2 | 3 |
| Blend Ratio (parts by weight)*5 | | | |
| Silicic anhydride | — | — | — |
| Hydrophobic silica*1 | 6 | 6 | — |
| Trimethylsiloxysilicic acid*2 | 1 | 9 | 9 |
| 1,3-butanediol | 1 | 1 | 1 |
| Neopentyl glycol dioctanoate | 3 | 3 | 3 |
| Nylon powder | 8 | 8 | 8 |
| Inorganic pigment | 2 | 2 | 2 |
| Mica titanium | 20 | 20 | 20 |
| Liquid paraffin | 2 | 2 | 2 |
| Sucrose fatty acid ester*6 | 6 | 6 | 6 |
| Parabens | 2 | 2 | 2 |
| Clay mineral*3 | — | — | 6 |
| Decamethylcyclopentasiloxane*4 | 49 | 41 | 41 |
| Viscosity (cp) | 30,000 | 40,000 | 40,000 |
| Eavaluation | | | |

TABLE 1-continued

| | | | |
|---|---|---|---|
| Use feeling | ○ | ○ | ○ |
| Cosmetic gather | | | |
| after 30 min | ○ | ○ | ○ |
| after 6 hr | ○ | ○ | ○ |
| Adhesive properties (water resistance) | ○ | ○ | ○ |
| Stability (40° C.) | | | |
| after 1 week | ○ | ○ | ○ |
| after 1 month | ○ | ○ | ○ |

*1 The hydrophobic silica was obtained by mixing silicic anhydride with polymethylphenylsiloxane (KF56, made by The Shin-Etsu Chemical Co., Ltd.), and then calcining the mixture at 300° C. for 2 hours.
*2 made by The Shin-Etsu Chemical Co., Ltd.
*5 The total of the blend ratio was 100 parts by weight.
*3 The clay mineral was obtained by treating bentnite with benzyldimethylstearylammonium chloride.
*4 made by The Shin-Etsu Chemical Co., Ltd.
*6 The sucrose fatty acid ester was obtained by esterification of sucrose with stearic acid and palmitic acid.

What is claimed is:

1. A liquid cosmetic composition comprising from 0.2 to 50 parts, by weight, of trimethylsiloxysilicic acid, from 5 to 80 parts, by weight, of a volatile silicone, from 1 to 20 parts, by weight, of a sucrose fatty acid ester selected from the group consisting of monoesters, diesters, triesters, tetraesters, pentaesters, hexaesters, heptaesters, octaesters, and mixtures thereof the fatty acids in said esters being selected from saturated and unsaturated fatty acids having from 1 to 28 carbon atoms; and a member selected from the group consisting of silicic anhydride having hydrophobic-treated surface, a clay mineral having organic-treated surface and mixtures thereof, the liquid cosmetic composition having a viscosity of 100,000 cp or less.

2. The liquid cosmetic composition according to claim 1 wherein the volatile silicone is selected from the group consisting of decamethylcyclopentasiloxane, dodecamethylcyclohexasiloxane, hexamethylcyclotrisiloxane and low molecular weight polymethylsiloxane, and mixtures thereof.

3. The liquid cosmetic composition according to claim 1 wherein the surface of the silicic anhydride is subjected to the hydrophobic treatment with a silicone selected from the group consisting of polymethylhydrogensiloxane, polymethylsiloxane, polymethylphenylsiloxane and mixtures thereof.

4. The liquid cosmetic composition according to claim 1 wherein the clay mineral is selected from the group consisting of bentonite, hectorite, montmorillonite and mixtures thereof.

5. The liquid cosmetic composition according to claim 1 wherein the surface of the clay mineral is subjected to the organic treatment with a cationic surface active agent selected from the group consisting of benzyldimethylstearylammonium chloride, dimethyldiacetostearylammonium chloride, distearyldimethylammonium chloride, benzalkonium chloride and mixtures thereof.

6. The liquid cosmetic composition according to claim 1 wherein 0.2 to 50 parts by weight of trimethylsiloxysilicic acid, 5 to 80 parts by weight of the volatile silicone, 1 to 20 parts by weight of the sucrose fatty acid ester, and 0.5 to 50 parts by weight of a member selected from the group consisting of the silicic anhydride having hydrophobic-treated surface, the clay mineral having organic-treated surface and the mixtures thereof are contained in 100 parts by weight of the liquid cosmetic composition.

7. The liquid cosmetic composition of claim 1 wherein the amount of trimethylsiloxysilicic acid is from 2 to 20 parts, by weight.

8. The liquid cosmetic composition of claim 1 wherein the volatile silicone is employed in amounts of from 10 to 60 parts, by weight.

9. The liquid cosmetic composition of claim 1, wherein the sucrose fatty acid ester is employed in amounts of from 2 to 10 parts, by weight.

\* \* \* \* \*